United States Patent [19]

Osamu

[11] Patent Number: 5,025,026
[45] Date of Patent: Jun. 18, 1991

[54] HAIR RESTORER

[75] Inventor: Nakaguchi Osamu, Toyonaka, Japan

[73] Assignee: Fujisawa Pharmaceutical Co., Ltd., Osaka, Japan

[21] Appl. No.: 400,118

[22] PCT Filed: Dec. 21, 1988

[86] PCT No.: PCT/JP88/01289

§ 371 Date: Aug. 21, 1989

§ 102(e) Date: Aug. 21, 1989

[87] PCT Pub. No.: WO89/05626

PCT Pub. Date: Jun. 29, 1989

[30] Foreign Application Priority Data

Dec. 24, 1987 [JP] Japan ................. 62-329227

[51] Int. Cl.$^5$ ........................... A61K 31/425
[52] U.S. Cl. .................................... 514/356
[58] Field of Search ........................... 514/356

[56] References Cited

U.S. PATENT DOCUMENTS 2,431,558 11/1947 Huber ................... 514/356
4,847,260 7/1989 Abe et al. ............... 514/356

*Primary Examiner*—Leonard Schenkman
*Attorney, Agent, or Firm*—Oblon, Spivak, McClelland, Maier & Neustadt

[57] ABSTRACT

This invention relates to a hair restorer comprising n-pentadecyl nicotinate as an active ingredient and has an outstandingly potent hair restorative action.

The hair restorer of this invention is manufactured by formulating n-pentadecyl nicotinate with a varying type of base such as an emulsion base, cream base, lotion base or hair tonic base in the per se conventional manner.

1 Claim, No Drawings

HAIR RESTORER

TECHNICAL FIELD

This invention relates to a hair restorer and more particularly to a hair restorer comprising n-pentadecyl nicotinate as an active ingredient.

BACKGROUND ART

A hair restorative action has been reported in esters of aliphatic alcohols containing an odd number of carbon atoms with aliphatic carboxylic acids, succinic acid, citric acid, fumaric acid, lactic acid, pyruvic acid, malic acid, oxaloacetic acid or phosphoric acid (Japanese Patent Publication Kokai No. 4113/1985).

However, the hair restorative action of these esters of aliphatic alcohols containing an odd number of carbon atoms is not sufficiently potent and none of them have ever been put to use.

DISCLOSURE OF THE INVENTION

The inventor of this invention found that n-pentadecyl nicotinate has an outstandingly potent hair restorative action as compared with the esters of aliphatic alcohols containing an odd number of carbon atoms as disclosed in Japanese Patent Publication Kokai No. 4113/1985 and has implemented the finding into this invention.

DESCRIPTION OF THE PREFERRED EMBODIMENTS

The hair restorer according to this invention comprises n-pentadecyl nicotinate as an active ingredient.

The hair restorer of this invention is manufactured by formulating n-pentadecyl nicotinate with a varying type of base such as an emulsion base, cream base, lotion base or hair tonic base in the per se conventional manner. The concentration of n-pentadecyl nicotinate in such varied formulations is not restricted but appropriately in the range of about 2 to 10 percent by weight for all practical purposes.

The hair restorer of this invention produces a synergistic effect when it contains, in addition to n-pentadecyl nicotinate, such other active ingredients as carpronium chloride, swertian herba extract, vitamin E nicotinate, etc. which have cutaneous peripheral vasodilating activity.

The following test example is intended to illustrate the efficacy of the hair restorer of this invention.

TEST EXAMPLE

METHOD

Male Japanese white rabbits (body weights 2.5–3.0 kg) were used as test animals. The back of each rabbit was clipped off hairs with an animal hair clipper and shaved with a razor. The individuals with island skin were culled out and the remaining animals were used in groups of 3.

From a sheet of filter paper (14.5 cm × 15.0 cm), disks with a diameter of 2 cm were cut out in a layout of 2 along the horizontal axis and 3 along the vertical axis with a uniform spacing of 1.5 cm.

This filter paper was set in position on the back of the test rabbit and six different test solutions were applied once a day to the skin areas corresponding to the cutouts. When hair growth was observed, its length was measured with calipers.

As test solutions, 1%, 5% and 10% solutions of n-pentadecyl nicotinate in 99.5% ethanol (test solutions A, B and C, respectively) were used. As control solutions, n-pentadecanoic acid glycerol ester, 99.5% ethanol and physiological saline (test solutions D, E and F, respectively) were used.

RESULTS

In the area treated with test solution B, hair growth was found on the 35th day after the beginning of application, and the length of hairs reached 4 mm on the 38th day.

In the area treated with test solution C, hair growth was found on the 36th day after the beginning of application.

None of the areas treated with the remaining test solutions showed hair growth till completion of the trial.

EXAMPLE 1 n-Pentadecyl nicotinate was dissolved in 99.5% ethanol to provide a 5% solution.

EXAMPLE 2 n-Pentadecyl nicotinate was dissolved in 99.5% ethanol to provide a 10% solution.

What I claim is:

1. A method of restoring hair in a subject in need thereof, which comprises administering to the subject an effective amount of n-pentadecyl nicotinate.

* * * * *